(12) United States Patent
Fackelmeier

(10) Patent No.: US 10,725,129 B2
(45) Date of Patent: Jul. 28, 2020

(54) METHOD FOR OPERATING A LOCAL COIL, LOCAL COIL, AND A MAGNETIC RESONANCE SCANNER

(71) Applicant: Siemens Healthcare GmbH, Erlangen (DE)

(72) Inventor: Andreas Fackelmeier, Thalmaessing (DE)

(73) Assignee: Siemens Healthcare GmbH, Erlangen (DE)

( * ) Notice: Subject to any disclaimer, the term of this patent is extended or adjusted under 35 U.S.C. 154(b) by 21 days.

(21) Appl. No.: 15/995,250

(22) Filed: Jun. 1, 2018

(65) Prior Publication Data
US 2018/0348315 A1 Dec. 6, 2018

(30) Foreign Application Priority Data
Jun. 2, 2017 (EP) .................................... 17174212

(51) Int. Cl.
| | | |
|---|---|---|
| *G01R 33/34* | (2006.01) | |
| *G01R 33/36* | (2006.01) | |
| *A61B 5/055* | (2006.01) | |
| *G01R 33/54* | (2006.01) | |
| *G01R 19/252* | (2006.01) | |

(52) U.S. Cl.
CPC ........ *G01R 33/34084* (2013.01); *A61B 5/055* (2013.01); *G01R 33/3607* (2013.01); *G01R 33/3621* (2013.01); *G01R 33/3685* (2013.01); *G01R 33/543* (2013.01); *G01R 19/252* (2013.01)

(58) Field of Classification Search
CPC .......... G01R 33/34084; G01R 33/3607; G01R 33/3685; G01R 33/543

USPC ......................................................... 324/309
See application file for complete search history.

(56) References Cited

U.S. PATENT DOCUMENTS

| | | | | |
|---|---|---|---|---|
| 5,936,498 A | * | 8/1999 | Takeshima | ......... G01R 33/3806 324/318 |
| 10,024,940 B2 | * | 7/2018 | Feiweier | ............ G01R 33/4833 |

(Continued)

FOREIGN PATENT DOCUMENTS

| | | |
|---|---|---|
| CN | 101283287 A | 10/2008 |
| CN | 104918547 A | 9/2015 |

(Continued)

OTHER PUBLICATIONS

"Manchester Code," Wikipedia (2018).
(Continued)

*Primary Examiner* — Reena Aurora
(74) *Attorney, Agent, or Firm* — Schiff Hardin LLP

(57) ABSTRACT

The invention relates to a method for operating a local coil for a magnetic resonance scanner, which has a receiving antenna and a signal converter, and is coupled to a patient table by a signal line in terms of signal communication. The receiving antenna receives an analog magnetic resonance signal in a first signal frequency range, wherein the analog magnetic resonance signal is converted into a digital magnetic resonance signal by the signal converter and is frequency-shifted such that the digital magnetic resonance signal is shifted into a second signal frequency range that does not overlap with, and is preferably higher than, the first signal frequency range.

10 Claims, 2 Drawing Sheets

(56) References Cited

U.S. PATENT DOCUMENTS

| | | |
|---|---|---|
| 2009/0121717 A1 | 5/2009 | Haans et al. |
| 2014/0218034 A1 | 8/2014 | Ishii et al. |
| 2014/0218035 A1 | 8/2014 | Okamoto |
| 2015/0285887 A1 | 10/2015 | Bollenbeck |
| 2018/0348315 A1 | 12/2018 | Fackelmeier |
| 2018/0348317 A1 | 12/2018 | Fackelmeier |

FOREIGN PATENT DOCUMENTS

| | | |
|---|---|---|
| CN | 104936518 A | 9/2015 |
| CN | 104977551 A | 10/2015 |
| EP | 3270177 A1 | 1/2018 |
| JP | 2006187405 A | 7/2006 |
| KR | 20180132547 A | 12/2018 |

OTHER PUBLICATIONS

Wippermann, "Eliminating Transmit and Receive Interference," PowerPoint Presentation at 17th Conference in Göhren on Rügen Island (2017).
Office Action dated Apr. 29, 2020 for Chinese Patent Application 201810562282.2.

\* cited by examiner

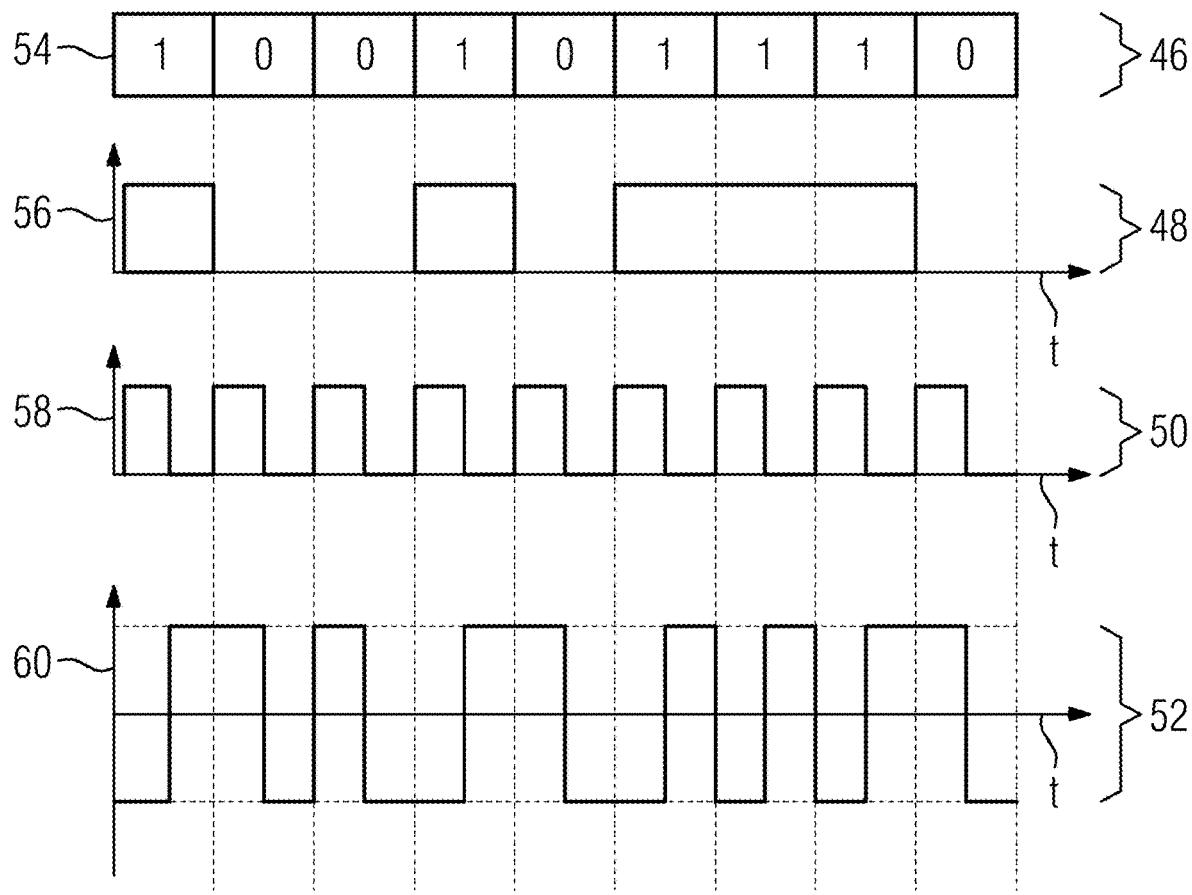

METHOD FOR OPERATING A LOCAL COIL, LOCAL COIL, AND A MAGNETIC RESONANCE SCANNER

BACKGROUND OF THE INVENTION

Field of the Invention

The invention concerns a method for operating a local coil of a magnetic resonance (MR) scanner that has a receiving antenna connected to a signal line, and a signal converter, wherein the signal line is coupled in terms of signal communication with a patient table, wherein the receiving antenna receives an analog magnetic resonance signal in a first signal frequency range. Furthermore, the invention concerns a local coil and a magnetic resonance scanner equipped with such a local coil.

Description of the Prior Art

A magnetic resonance scanner typically has a patient table for receiving a patient thereon for examination, which is positioned and/or can be positioned in a cylindrical data acquisition area. In the data acquisition area, a strong (static) magnetic field that is generated in operation during a magnetic resonance examination by a basic filed magnet. The scanner also has a radio-frequency transmitting antenna, and gradient coils that are activated to produce magnetic field gradients for spatially encoding and reading out the MR signals. During operation, nuclear spins of atoms in the body of the patient are excited by an alternating magnetic field radiated by the RF transmitting antenna at a magnetic resonance frequency (Larmor frequency). The Larmor frequency means the (precession) frequency of the specific nuclear spin in the specific (static) magnetic field strength of the magnetic resonance scanner. The precessing (excited) nuclear spins, after excitation thereof, relax so as to return to the steady state imposed by the basic magnetic field. During that relaxation of the nuclear spins, they emit RF signals (MR signals) that are detected by the same antenna that produced the excitation, or by a different reception coil or coils. The detected MR signals (raw data) are then transformed into image data in a known manner.

In such a magnetic resonance examination, usually local coils, which are positioned in the vicinity of the body area of the patient for examination, are used for signal detection of these magnetic resonance signals.

The local coils typically have receiving antenna assemblies having at least one, but frequently several receiving antenna, usually in the form of conductor loops. Usually, the received analog magnetic resonance signals are pre-amplified in the local coil by a signal converter and are conducted from the central area of the magnetic resonance scanner via signal lines, and supplied to a shielded receiver of a signal processor of the magnetic resonance scanner.

The transfer of the magnetic resonance signals (raw data) generally takes place from the local coil to the patient table and from the latter to the signal processor. The electrical or electronic components of the local coil are designed to be as energy-efficient as possible in order to avoid unwanted heat losses from being generated. Moreover, the components are preferably non-magnetic so that they do not affect the magnetic resonance signals to be received. Furthermore, the transmitted magnetic resonance signals in the signal frequency range of the received magnetic resonance signals should not generate any interfering signals as far as possible.

For signal transmission of the received magnetic resonance signals, it is conceivable, for example, for the analog magnetic resonance signals of the receiving antenna to be converted into digital magnetic resonance signals. Local coils, in which the magnetic resonance signals are digitized, are referred to as digital local coils. Such digital local coils have, for example, FPGAs (Field Programmable Gate Arrays) or signal buffer modules for generating digital magnetic resonance signals.

A transfer of the digitized magnetic resonance signals from the local coil to the patient table would be technically feasible with comparative ease in a baseband and furthermore, the electronic components involved have a reduced consumption of energy.

Disadvantageously, however, with such digitization powerful signal components develop over a large signal frequency range from a few Hz (Hertz) up to the range of GHz. As a result, the signal frequency range of the digitized magnetic resonance signals overlaps the signal frequency range of the (analog) magnetic resonance signals to be received. Consequently, the digitized magnetic resonance signals are typically strong interfering signals with respect to the magnetic resonance signals of the receiving antennae to be received, which frequently cannot be sufficiently attenuated by shielding of the signal lines. Furthermore, it is problematic that comparatively complex and costly standing wave traps are required for the signal lines in the signal frequency range of the digitized magnetic resonance signals.

SUMMARY OF THE INVENTION

An object of the present invention is to provide a suitable method for operating a magnetic resonance scanner. In particular, a reliable signal transmission of digitized magnetic resonance signals from a local coil to a patient table, which does not adversely affect the reception of analog magnetic resonance signals is to be enabled. A further object of the invention is to provide a suitable local coil and a magnetic resonance scanner with such a local coil.

The method according to the invention is designed for operating an imaging magnetic resonance scanner. The magnetic resonance scanner has at least one local coil that is coupled, for signal communication, with the patient table via a signal line. Furthermore, the digital local coil has a receiving antenna and a signal converter.

During the operation of the magnetic resonance scanner, in other words, during a magnetic resonance examination, analog magnetic resonance signals are received by the receiving antenna. The analog magnetic resonance signals have a first signal frequency range, which essentially corresponds to the frequency range of the magnetic resonance frequencies and thus the Larmor frequencies.

The analog magnetic resonance signal is converted into a digital magnetic resonance signal by the signal converter, and during this conversion is frequency-shifted so that the digital magnetic resonance signal is shifted into a second signal frequency range that does not overlap with, and is preferably higher than, the first signal frequency range. In other words, compared to the analog magnetic resonance signal, the digital magnetic resonance signal is increased with regard to its signal frequency, so the digital magnetic resonance signal does not generate any interfering signals in the frequency range of the analog magnetic resonance signals to be received in a transfer by way of the signal line. The second signal frequency range has a certain minimum frequency interval with respect to the first signal frequency range so as to reliably ensure that no interference is generated in the first signal frequency range during the transfer of the digital magnetic resonance signals. In this way, a particularly suitable method for operating the magnetic resonance scanner is achieved.

For example, for a magnetic resonance scanner with a magnetic field strength of 1.5 T (tesla), magnetic resonance frequencies (for hydrogen nuclear spins) occur at approximately 63.6 MHz (megahertz), for a magnetic resonance scanner with a magnetic field strength of 3 T at approximately 123.2 MHz, and for a magnetic resonance scanner with a magnetic field strength of 7 T at approximately 297.8 MHz. The range of magnetic resonance frequencies arising, i.e., the magnetic resonance signals, is appropriately a few megahertz. Preferably the first signal frequency range ranges from 0 to 600 MHz, in particular, from 0 to 300 MHz.

In an embodiment, line coding and/or signal modulation are used for frequency shifting of the digital magnetic resonance signals. Line coding means an assignment of a particular (signal) level sequence to a bit sequence in the data stream (bit stream). This ensures particularly suitable signal transmission. The digital magnetic resonance signal is not frequency-shifted by mixing, but by line coding and/or signal modulation. This dispenses with the need for local oscillators, so the structure of the signal converter and/or the local coil is simplified.

In another embodiment, the received magnetic resonance signals of the receiving antenna are down-mixed. These analog signals are then digitized. The resulting frequency spectrum has a high signal level at 0 Hz. This signal level is shifted to higher frequencies by means of line coding and/or signal modulation. The digital magnetic resonance signal to be transmitted can be adapted by such line coding by specific deformation of the signal spectrum or shifting of the signal frequency range to the signal line and the magnetic resonance frequencies and Larmor frequencies arising.

Appropriate codes for line coding are, for example, ternary codes such as bipolar return-to-zero codes (RZ code) such as RZ-AMI (Return to Zero-Alternate Mark Inversion). In such line coding, a (data)bit stream for transmission is coded for data transfer by means of three different (signal) level values which are referred to as "+1", "0" and "−1". The logic-0 states of the bit stream are transmitted with the level "0" here, wherein the logic-1 states of the bit stream are transmitted alternatingly with the levels "+1" and "−1".

Furthermore, it is conceivable for a code to be used for a simple and secure clock recovery such as, for example, a High Density Bipolar code (HDBn Code), in particular, a HDB3 code (High Density Bipolar code of the third order). HDBn code is based on an AMI code in which, however, long zero sequences can lead to a loss of synchronization. To avoid such losses of synchronization, code violation rules are used for HDBn code. For an HDB3 code, for example, the fourth zero ("0") in succession is replaced by a one ("+1", "4") in reverse polarity.

Further possible codes are, for example, Bipolar With 8 Zeros Substitution (B8Z2) code, Miller code or Manchester code, and other biphasic codes. The B8Z2 code prevents a loss of synchronization in a long bit stream of zeros. With a Miller code (delay code) and/or in a digital frequency modulation, after each payload data bit (logic-1, logic-0) a signal change takes place between two level values. In a logic-1 bit, a signal change also takes place in the bit center. With the Manchester code, the data signal is given a clock signal in coding. A bit sequence modulates the phase position of the clock signal in binary fashion for this purpose. In other words, the edges of the coded signal, with regard to the clock signal, carry the information.

Likewise, Non-Return-to-Zero codes (NRZ code) with a scrambling of the data signal, thus with a replacement of bit sequences in data transmission by bit sequences which are better adapted to the properties of the transmission channel of the signal line, are conceivable.

Furthermore, it is possible that beyond ternary coding, multilevel Pulse Amplitude Modulation (PAM) is used to improve the data rate. This achieves particularly effective and efficient signal modulation with regard to the spectral power distribution of the digital magnetic resonance signals.

The (digital) local coil according to the invention is suitable and equipped for use in a magnetic resonance scanner. The local coil has at least one receiving antenna which is connected to a signal converter. A signal line is supplied to the signal converter via which the local coil is coupled in terms of signal communication to the patient table of the magnetic resonance scanner.

In the assembled state the local coil is suitable and configured to perform the method according to the invention described above. To this end, the local coil has, for example, a controller integrated into the signal converter which is generally configured—in terms of programs and/or circuitry—to perform the method described above. The controller is thus specifically configured to digitize the analog magnetic resonance signals with the first signal frequency range and in particular, to feed them into the signal line as digital magnetic resonance signals with the second signal frequency range with line coding and/or signal modulation.

In an embodiment, at least in essence, the controller comprises a respective microcontroller with a processor and a memory in which the functionality to perform the method according to the invention is implemented by programming in the form of operating software (firmware) so that the method—if need be, in interaction with a user of the scanner—is performed automatically during execution of the operating software in the microcontroller.

In the context of the invention, however, alternatively the controller may also have non-programmable components, for example, application-specific integrated circuits (ASICs) in which the functionality to perform the method according to the invention is implemented with circuitry.

In a preferred embodiment, the signal converter has a logic and/or digital module for frequency shifting of the digital magnetic resonance signals. In other words, the controller is designed as a logic module, in particular, wherein the code for line coding is preferably adjusted to the logic module so that the latter can be implemented with particular ease. Thus, for example, a Manchester coding can be achieved with ease by means of an EXOR linking of the clock with the bit stream. This means that the raising of the signal frequencies is based on a coding of the baseband bit stream of the digital magnetic resonance signal with the aid of the logic module. In particular, no up-mixing of the magnetic resonance signals therefore takes place in the second signal frequency range by means of mixer modules.

Contrary to the prior art, in which FPGAs (Field Programmable Gate Arrays) or signal buffer modules are used, in the digital local coil according to the invention only a logic or gate module, for example, an IC with six pins, is required. As a result, the signal converter has particularly low energy consumption and a particularly small space requirement. Moreover, interfering influences as a result of the received magnetic resonance signals are avoided and problems as a result of magnetic materials in the components of the local coil are advantageously reduced. This facilitates a particularly suitable local coil for a magnetic resonance scanner.

In an embodiment, a high-pass filter for attenuating signal frequencies of the digitized magnetic resonance signal outside the second signal frequency range is arranged between the signal converter and the signal line. The high-pass filter is, for example, arranged on the outlet side on the signal converter. After line coding, it is possible that the digitized magnetic resonance signal still has signal components in a frequency range between 0 Hz and the magnetic resonance frequency, and can thus interfere with the reception of the receiving antenna in a transfer.

By filtering out these interfering signal components, the digital coded magnetic resonance signal is only changed slightly, but without adverse affecting transmission via the signal line. The high-pass filter is therefore particularly suitable and equipped to let through signals or signal components in the second signal frequency range and to attenuate signals or signal components in the first signal frequency range. In other words, the transmission range of the high-pass filter essentially corresponds to the second signal frequency range, thus enabling particularly effective and reliable signal transmission.

In an embodiment, the signal line is designed as a symmetrical two-wire line with a number of standing wave traps that form a symmetrical high-pass line. In this way, the reliability of signal transmission is further improved. The method according to the invention is advantageously transferred to a simplified design of the standing wave trap, whereby the signal line has a small line diameter and a reduced construction weight.

In another embodiment, the signal line also has a shield. The standing wave traps have appropriately discrete high-pass filters of a higher order which are discrete or designed with distributed components, with capacitors and coils on boards and/or circuit boards. The standing wave traps are introduced into the signal line at fixed intervals to one another to form the high-pass line. In the transmission range of this high-pass line, the digital magnetic resonance signals are transmitted from the local coil to the patient table, wherein on the second line control and clock signals are supplied from the patient table to the local coil in the opposite direction.

In another embodiment, energy is transmitted to the local coil combined with the signal line or via a separate line, with which a low pass or a band-stop filter is inserted at the position of the standing wave traps.

In an advantageous embodiment, the signal line has a signal terminal or signal connector which is designed at least partially for wireless signal transmission to the patient table. In a suitable embodiment, the signal terminal is, in particular, designed as a contactless NFC connector (Near Field Communication). In this way, a particularly expedient coupling between the local coil and the patient table is achieved in terms of signaling which, in particular, is conducive to a reduction in the number of contacts in the plug connector.

In a preferred application, the local coil is used in a magnetic resonance scanner and coupled and/or connected to the patient table by means of the signal line in terms of signaling. A particularly suitable and energy-efficient magnetic resonance scanner is realized by the local coil according to the invention.

BRIEF DESCRIPTION OF THE DRAWINGS

FIG. 3 is a coding diagram of a data signal using a Manchester code.

DESCRIPTION OF THE PREFERRED EMBODIMENTS

Figure 1:
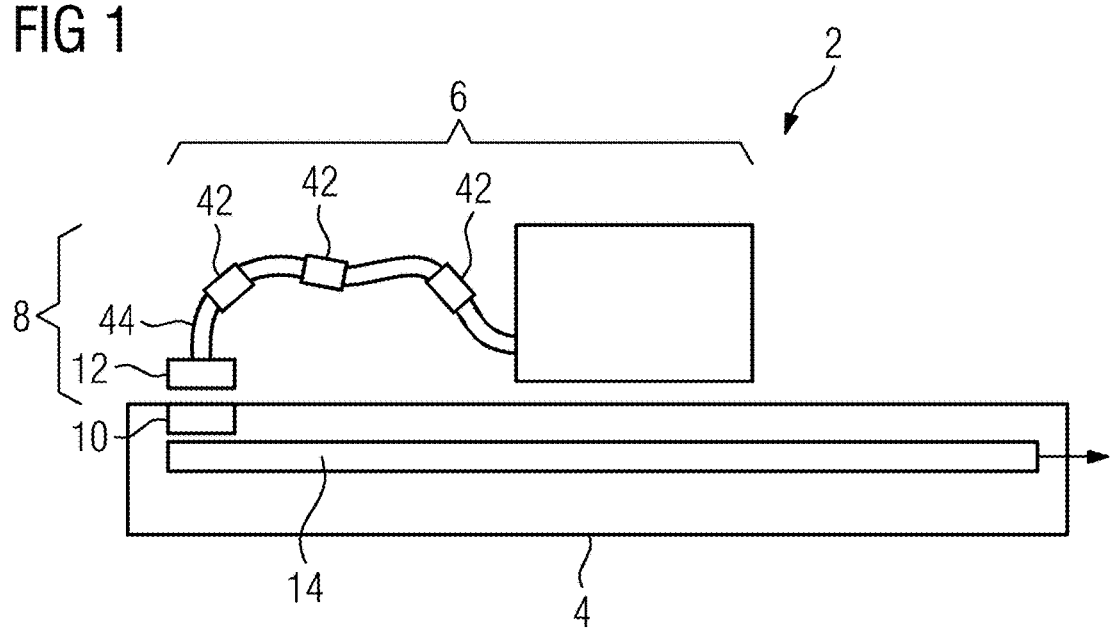
FIG. 1 schematically illustrates a portion of a magnetic resonance scanner with a patient table and with a local coil.

Correlated parts and dimensions always have the same reference characters in all the figures.

FIG. 1 shows a view of a portion of imaging magnetic resonance scanner 2 with a patient table 4 and a digital local coil 6. The local coil 6 is coupled to the patient table 4 by means of a signal line 8 in terms of signaling.

The patient table 4 has a line connection 10 for a signal terminal 12 of the signal line 8 which is supplied to an integrated data line 14. The signal terminal 12 is, for example, designed as a wireless and/or contactless NFC connector. The data line 14 is supplied on the outlet side, for example, by means of a table foot connector, to a signal processing device not shown, by means of which the image data received during the operation of the local coil 6 is evaluated and optically presented.

Figure 2:
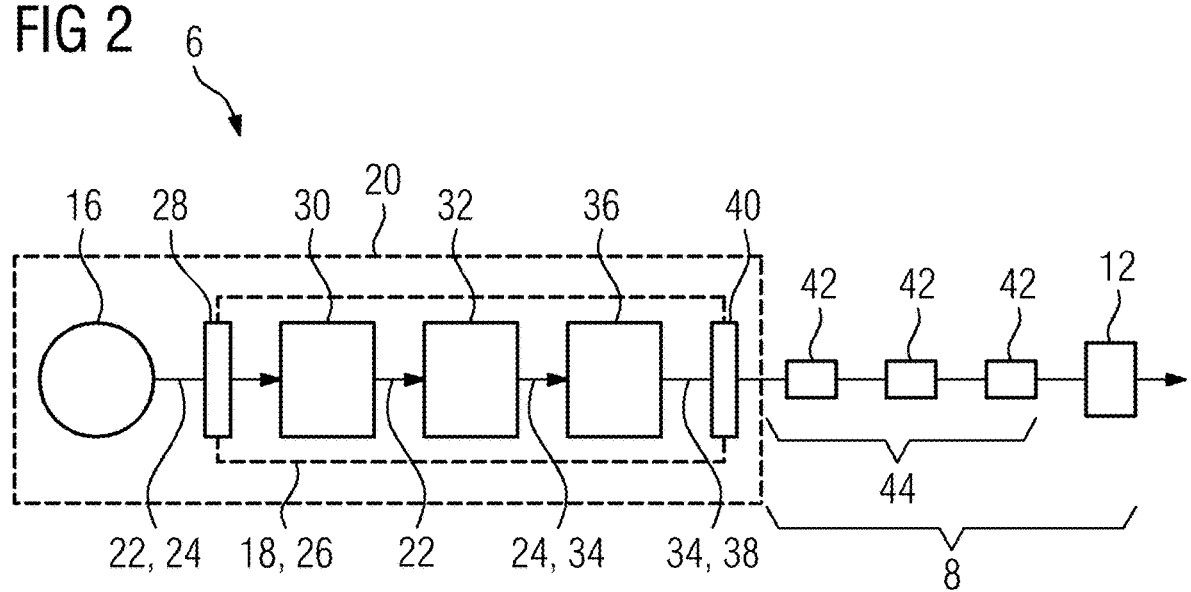
FIG. 2 is a block diagram of the local coil with a receiving antenna and with a signal converter and with a signal cable in accordance with the invention.

The local coil 6 shown individually in FIG. 2 has at least one receiving antenna 16 and one signal converter 18 supplied to the signal line 8. The receiving antenna 16 and the signal converter 18 are, for example, arranged in a mat or a housing 20 from which the signal line 8 protrudes.

During operation, in other words, during a magnetic resonance examination, the mat 20 of the local coil 6 is positioned close to the region for examination and/or close to the volume for examination so that the receiving antenna 16 is as close as possible. The receiving antenna 16 receives analog magnetic resonance signals 22 in a first signal frequency range 24 from this region as image data and supplies these to the signal converter 18. The signal frequency range 24 extends in a small, comparatively narrow-band, frequency range around the magnetic resonance frequency of the magnetic resonance scanner 2. This means that the signal frequency range 24 essentially corresponds to the frequency range of the magnetic resonance frequencies and/or Larmor frequencies arising.

The signal converter 18 has a high-frequency housing (high-frequency shield housing) 26. On the inlet side the signal converter 18 has a band-pass filter 28 with its transmission range adapted to the signal frequency range 24. The band-pass filter 28 is supplied to a multiplexer 30 by which, particularly in the case of several receiving antennae 16, several analog signal channels are multiplexable. The analog magnetic resonance signal 22 is then supplied to an analog-to-digital converter 32 and converted into a digital magnetic resonance signal 34.

The digital magnetic resonance signal 34 is then sent to a controller or logic module 36 by means of which the magnetic resonance signal 34 is frequency-shifted. The magnetic resonance signal 34 is coded by means of signal and/or line coding (FIG. 3), and its frequency range thus increased to a second signal frequency range 38. The signal frequency range 38 of the digital magnetic resonance signal 34 does not overlap with the signal frequency range 24 of the analog magnetic resonance signal 22. In other words, the baseband bit stream of the magnetic resonance signal 34 is increased by means of the coding of the logic module 36 such that the magnetic resonance signal 34 can be transmitted to the patient table 4 with the signal line 8 without interfering with the magnetic resonance reception of the receiving antenna 16.

To ensure that the transmitted magnetic resonance signal 34 does not have any signal components in the first signal resonance range 24, the magnetic resonance signal 34 at the outlet of the signal converter 18 is fed into the signal line 8 by means of a high-pass filter 40. The transmission band of the high-pass filter 40 is adapted to the signal frequency range 38 of the magnetic resonance signal 34, in particular, signal frequencies from the first signal frequency range 24 are filtered and/or attenuated.

The signal line 8 is designed as a shielded, symmetrical two-wire line, wherein in FIG. 2 only one of the wire lines is shown diagrammatically. The signal line 8 has a number of standing wave traps 42, wherein in the figures only three standing wave traps 42 are shown by way of example in each case. The standing wave traps 42 are inserted at fixed intervals in the signal line 8 and form a symmetrical high-pass line 44 which is supplied to the signal terminal 12.

The signal terminal 12 is, for example, designed as a Near Field connector for at least partially wireless signal transmission to the patient table 4.

FIG. 3 shows an example of line coding with a Manchester code. The diagram in FIG. 3 comprises four horizontal sections arranged one above the other 46, 48, 50, 52. The time t is applied horizontally, in other words, on the x-axis or abscissa.

In the upper section 46 of FIG. 3 a bit signal or bit stream 54 for coding with five logic-1 states and four logic-0 states is shown as a rectangular box. A corresponding digital signal 56, for example, the digitized magnetic resonance signal 34 with the signal frequency range 24, in which the logic-1 states have a high signal level and the logic-0 states a low signal level, is shown in the section 48.

A clock signal 58 is shown in the section 50, wherein in the lower section 52 a data signal 60 coded on the basis of the clock signal 58 is shown which, for example, can be transmitted as a digitized magnetic resonance signal 34 with the signal frequency range 38.

In the line coding shown by means of the Manchester code, the phase position of the clock signal 58 is modulated by means of the data signal 56 in a binary fashion such that a falling edge of the data signal 60 describes a logic-0 state and a rising edge a logic-1 state of the bit stream 54. The Manchester coding shown is, for example, implemented with ease by means of EXOR linking of the logic module 36 through linking of the clock signal 58 with the bit stream 54 and/or digital signal 56.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for operating a local coil of a magnetic resonance scanner, said magnetic resonance scanner comprising a patient table and said local coil comprising a reception antenna and a signal converter connected thereto, with said signal converter being connected to a signal line that is coupled for signal communication to the patient table, said method comprising:

during operation of the magnetic resonance scanner, receiving an analog magnetic resonance signal with said reception antenna in a first signal frequency range;

in said signal converter, that is comprised within the local coil, converting the analog magnetic resonance signal into a digital magnetic resonance signal with frequency shifting that shifts the digital magnetic resonance signal into a second signal frequency range that does not overlap with said first signal frequency range; and transmitting the frequency-shifted digital magnetic resonance signal via the signal line to the patient table.

2. A method as claimed in claim 1 wherein said second signal frequency range is higher than said first signal frequency range.

3. A method as claimed in claim 1 comprising frequency shifting the digital magnetic resonance signal in said signal converter by a frequency shift procedure selected from the group consisting of line coding and signal modulation.

4. A local coil for use in a magnetic resonance scanner comprising a patient table, said local coil comprising:

a reception antenna a signal converter connected to said reception antenna, wherein said signal converter connected to a signal line that is coupled for signal communication to the patient table;

during operation of the magnetic resonance scanner, said reception antenna receiving an analog magnetic resonance signal in a first signal frequency range; and said signal converter being configured to convert the analog magnetic resonance signal into a digital magnetic resonance signal with frequency shifting that shifts the digital magnetic resonance signal into a second signal frequency range that does not overlap with said first signal frequency range, and to transmit the frequency-shifted digital magnetic resonance signal via the signal line to the patient table.

5. A local coil as claimed in claim 4 wherein said signal converter comprises a logic module that implements said frequency shifting.

6. A local coil as claimed in claim 4 comprising a high-pass filter connected between said signal converter and said signal line, said high-pass filter attenuating signal frequencies of said digitized magnetic resonance signal that are outside of said second signal frequency range.

7. A local coil as claimed in claim 4 wherein said signal line is a symmetrical two-wire line comprising a plurality of standing wave traps, and thereby forming a symmetrical high-pass line.

8. A local coil as claimed in claim 7 wherein said signal terminal is a contact list Near Field Communication (NFC) connector.

9. A local coil as claimed in claim 4 wherein said signal line comprises a signal terminal configured for wireless signal communication with said patient table.

10. A magnetic resonance apparatus comprising:

a magnetic resonance scanner comprising a patient table;

a local coil comprising a reception antenna and a signal converter connected thereto, wherein said signal converter is connected to a signal line that is coupled for signal communication to the patient table;

during operation of the magnetic resonance scanner, said reception antenna receiving an analog magnetic resonance signal in a first signal frequency range; and said signal converter being configured to convert the analog magnetic resonance signal into a digital magnetic resonance signal with frequency shifting that shifts the digital magnetic resonance signal into a second signal frequency range that does not overlap with said first signal frequency range, and to transmit the frequency-shifted digital magnetic resonance signal via the signal line to the patient table.

\* \* \* \* \*